United States Patent [19]

Kensey et al.

[11] Patent Number: 5,097,849

[45] Date of Patent: * Mar. 24, 1992

[54] METHOD OF USE OF CATHETER WITH WORKING HEAD HAVING SELECTABLE IMPACTING SURFACES

[75] Inventors: Kenneth Kensey, Chester Springs; John Nash, Downingtown, both of Pa.

[73] Assignee: Kensey Nash Corporation, Exton, Pa.

[ * ] Notice: The portion of the term of this patent subsequent to Aug. 27, 2008 has been disclaimed.

[21] Appl. No.: 546,073

[22] Filed: Jun. 29, 1990

Related U.S. Application Data

[63] Continuation-in-part of Ser. No. 395,109, Aug. 17, 1989, Pat. No. 5,042,984.

[51] Int. Cl.$^5$ .............................................. A61B 17/22
[52] U.S. Cl. .................................. 128/898; 606/159; 606/180
[58] Field of Search ............... 606/127, 128, 160, 161, 606/162, 168, 171, 180, 170, 159; 128/898; 604/22

[56] References Cited

U.S. PATENT DOCUMENTS 4,700,705 10/1987 Kensey et al. ..................... 606/159

Primary Examiner—Michael H. Thaler
Attorney, Agent, or Firm—Caesar, Rivise, Bernstein, Cohen & Pokotilow, Ltd.

[57] ABSTRACT

A catheter and method of use for engaging material within the body of a living being to accomplish a medical and/or surgical procedure, e.g., form and enlarging an opening in a restriction in a vessel, duct, or lumen formed by the material, or to destroy a stone or other hard body formed of the material. The catheter comprises an elongated body portion and a rotatable working head located at the distal end of the catheter. The catheter is positioned with the working head adjacent the material to be enlarged. The working head comprises at least two, non-sharp, impacting surfaces, each of differing aggressiveness of restriction opening action. The less aggressive of the impacting surfaces is brought into engagement with the material when the working head is rotated in one rotational direction. The more aggressive of the impacting surfaces is then rotated in the opposite rotational direction and brought into engagement with the material to complete the procedure.

17 Claims, 2 Drawing Sheets

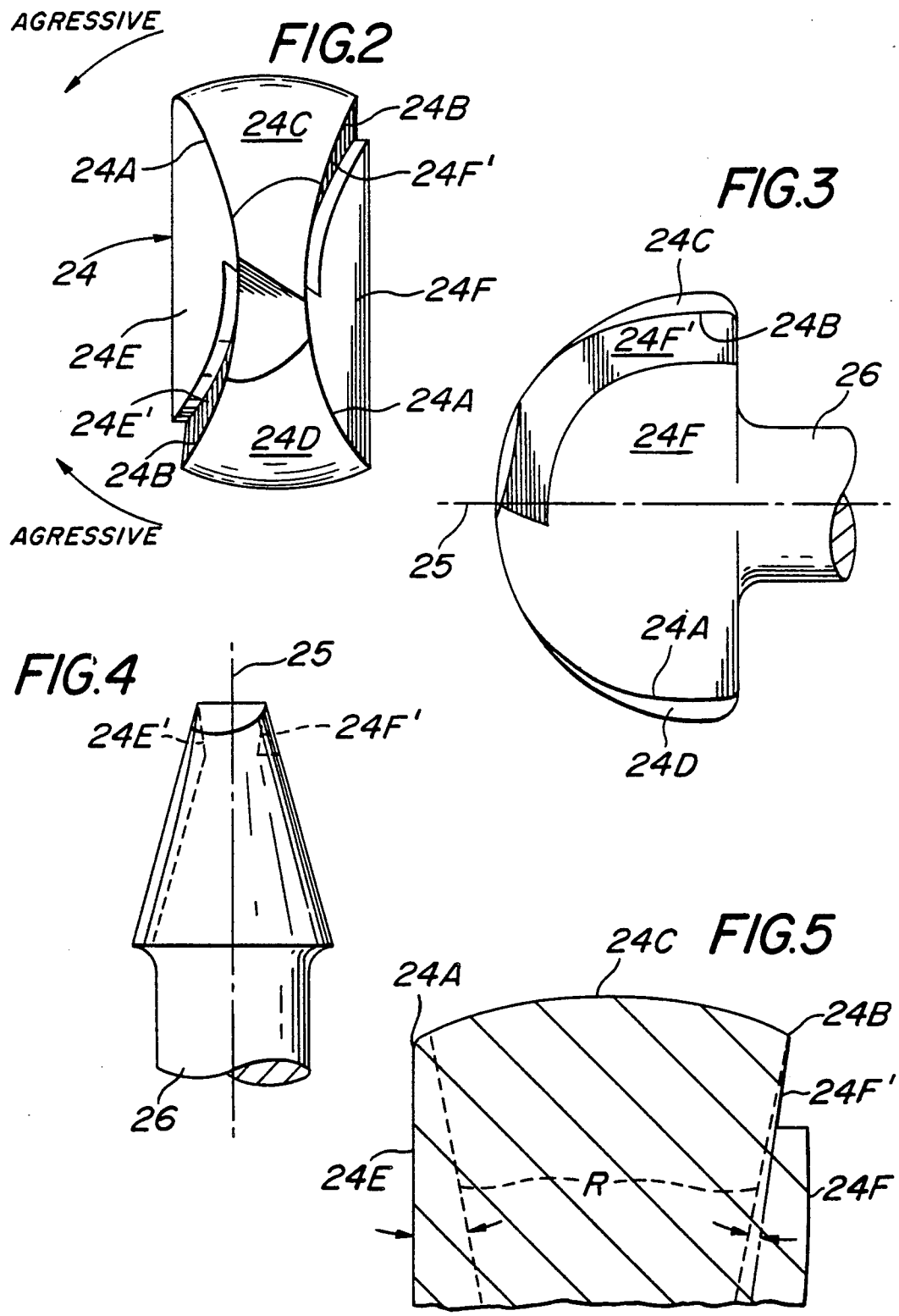

METHOD OF USE OF CATHETER WITH WORKING HEAD HAVING SELECTABLE IMPACTING SURFACES

This application is a Continuation-In-Part of our earlier application Ser. No. 395,109, now U.S. Pat. No. 5,042,984, filed on Aug. 17, 1989, entitled Catheter With Working Head Having Selectable Impacting Surfaces, which is assigned to the same assignee as this invention and whose disclosure is incorporated by reference herein.

This invention relates generally to medical instruments and their methods of use, and more particularly to catheters and methods of use for enlarging openings in vessels, ducts, or lumens, in living beings.

BACKGROUND OF THE INVENTION

Various types of catheter instruments have been suggested or disclosed in the patent literature for effecting non-invasive or minimally invasive surgical or medical procedures within the body of a person or animal. For example, in U.S. Pat. No. 4,445,509 (Auth) there is disclosed a recanalization catheter designed specifically for cutting away hard, abnormal deposits, such as atherosclerotic plaque from the inside of an artery while supposedly preserving the soft arterial tissue. That recanalizing catheter includes a sharp-edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon relatively hard deposits are cut away from relatively soft tissue. Suction ports are provided in the cutting tip to pull the hard particles produced by the cutting action into the catheter for removal at the proximal end thereof so that such particles thereof so that such particles do not flow distally of the catheter where they could have an adverse effect on the patients' body.

It has been determined that the use of sharp rotary cutting blades in a revascularization catheter can have various adverse effects on arterial tissue, e.g., snagging, cutting, or otherwise damaging the tissue of the artery wall.

In our U.S. Pat. No. 4,700,705 (Kensey et al.), assigned to the same assignee as this invention, and whose disclosure is incorporated by reference herein, there is disclosed and claimed catheters and methods of use for effecting the opening of a vessel, duct or lumen, such as the opening of a atherosclerotic restriction in an artery or the opening of a fallopian tube. The catheters of that invention consist of elongated flexible members of sufficient flexibility to enable them to be readily passed through the body of the patient to the situs of the procedure to be accomplished, e.g., the location of the atherosclerotic plaque in the artery to be opened. A working head is mounted at the distal end of the catheter and is arranged for high-speed rotation about the longitudinal axis of the catheter. In some embodiments the catheter may eject fluid at the working head to expedite the procedure.

In another of our U.S. patents, namely, U.S. Pat. No. 4,747,821 (Kensey et al.) (hereinafter referred to as the '821 patent), also assigned to the same assignee as this invention and whose disclosure is incorporated by reference herein, there is disclosed and claimed other catheters particularly suited for revascularization of arteries.

Each of those catheters includes a rotary working head having at least one non-sharp impacting surface to effect material removal without cutting. Moreover, those catheters are arranged to eject fluid adjacent the working head to expedite the procedure. When such a catheter is used for treating atherosclerotic disease by recanalizing arteries, the catheter is guided through the vascular system of the patient to the site of the vascular occlusion or blockage (restriction) that has been determined to exist so that the rotary working head is located immediately adjacent the restriction. The working head is then rotated about the longitudinal axis of the catheter at a high rate of speed, e.g., from 10,000 rpm to 200,000 rpm. At the same time, fluid is passed through the catheter and out of its distal end adjacent the working head.

The opening of the restriction to allow freer flow of blood is effected by the dilation and/or selective emulsification properties of the catheter's working head. In this connection, during the rotation of the working head fluid jets exiting the distal end of the catheter at the working head or immediately accelerated laterally by portions of the working heads so that they are broken up into small segments that develop considerable momentum as they are flung out in all directions, including radial directions, toward the wall of the artery. These liquid segments transfer their momentum to the artery wall, forcing the artery wall outward laterally in all directions thereby aiding in dilating it. Moreover, the radial pressure developed by the rotating working head is substantial and can raise local static pressure immediately adjacent the working head by approximately 100 to 200 millimeter of Hg. This increased pressure on the artery wall contiguous with the rotating working head is not due solely to the impact of the liquid segments thereon, but also due to the recirculation of the liquid surrounding the working head. In this connection, the rotation of the working head produces a powerful, toroidal shaped vortex contiguous with the working head.

The vortex, in addition to augmenting the application of increased pressure to the artery wall contiguous with the working head, also has the effect of recirculating any particles that may have been broken off from the material forming the arterial restriction by the impact of the rotary working head with that material. In particular, the working head, with its non-sharp impacting surfaces differentiates atherosclerotic tissue from normal tissue through the inherent differences in the tissues' physical properties and organizational patterns. Therefore, when the catheter is passed transluminally through the diseased artery, its working head serves to emulsify occlusive lesions not covered with fibrous plaque by repeatedly impacting the material forming the restriction as the working head is rotated, and with minimal risks of puncture or perforation of the contiguous artery wall. The emulsification process is accomplished by the repeated impaction of the non-sharp impacting surfaces on the material forming the restriction. This action causes the material to be broken away in small particles. The vortex flow at the working head insures that any particles produced by the impacting action are drawn back into contact with the impacting surfaces of the rotating working head. Accordingly, those particles are repeatedly impacted over and over, with each impaction reducing the size of the particles further until the resulting particle size is sufficiently small, e.g., 95% have a surface area less than that of a red-blood cell, that they can be permitted to flow to downstream tissue without causing any significant deleterious effects to the patient.

Other catheters for enlarging an opening in a vessel, duct or lumen have been disclosed and claimed in the following United States patents, assigned to the same assignee of this invention, and whose disclosures are also incorporated by reference herein: U.S. Pat. No. 4,589,412 (Kensey); U.S. Pat. No. 4,631,052 (Kensey), U.S. Pat. No. 4,686,982 (Kensey et al.), U.S. Pat. No. 4,749,376 (Kensey et al.) and U.S. Pat. No. 4,790,813 (Kensey).

For some procedures involving the enlarging of openings in vessels, ducts and lumens, it may prove beneficial or more effective to utilize catheters whose working heads include impacting surfaces of differing aggressiveness which may be selectively brought into engagement with the restriction to be opened. Moreover, such catheters can be utilized to effect other procedures within the body of a living being, e.g., the destruction of stones or other hard bodies. Examples, of other prior catheters and/or instruments for destroying stones within the body of a living being are the following which are assigned to the same assignee as this invention: U.S. Pat. No. 4,679,558 (Kensey et al.) and U.S. Pat. No. 4,811,735 (Kensey et al.).

In our aforementioned application there is disclosed and claimed methods of revascularizing partially or fully occluded arteries utilizing a rotating working head having at least two impacting surfaces, one of more aggressiveness than the other. The subject invention relates to such methods.

OBJECTS OF THE INVENTION

Accordingly, it is the general object of this invention to provide a method of use of an instrument for revascularizing partially or totally occluded arteries in living beings.

It is a further object of this invention to provide a method of use of an instrument which includes a rotary working head having at least two non-sharp impacting surfaces each of which exhibits a different aggressiveness in action when brought into engagement with material in the artery forming the occlusion.

It is yet a further object of this invention to provide a method of use of an instrument which includes a rotary working head having at least two non-sharp impacting surfaces, one of which exhibits less aggressiveness in action when brought into engagement with a relatively soft material, e.g., a thrombus, forming the occlusion, and the other of which exhibits more aggressiveness in action when brought into engagement with a relatively hard material, e.g., calcific tissue, forming the occlusion.

SUMMARY OF THE INVENTION

These and other objects of the instant invention are achieved by providing a method of recanalizing an artery located in the body of a living being utilizing an instrument comprising an elongated body portion and a moveable working head. The artery is partially or fully occluded by material located therein, with the material comprising at least one, relatively soft or relatively hard, component. The working head is arranged for rotation about a longitudinal axis of the instrument and comprises a first non-sharp, impacting surface exhibiting a first predetermined aggressiveness of action when engaging material comprising the relatively soft component, and a second non-sharp, impacting surface exhibiting a second and greater predetermined aggressiveness of action when engaging material comprising the relatively hard component.

The method comprises introducing the instrument into the body so that the working head is adjacent the material. The working head is rotated about the axis. The first impacting surface is brought into engagement with the material as the head is rotated if the material comprises the relatively soft component. Alternatively, the second impacting surface is brought into engagement with the material as said head is rotated about the axis if the material comprises the relatively hard component.

In accordance with one preferred method the catheter is used with its working head rotating in one direction to produce the less aggressive revascularization action and is rotated in the opposite direction to produce the more aggressive revascularization action.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 2 is an enlarged front elevational view of the working head shown in FIG. 1;

FIG. 3 is an enlarged side elevational view of the working head shown in FIG. 1;

FIG. 4 is an enlarged top elevational view of the working head shown in FIG. 1; and FIG. 5 is a greatly enlarged, transverse (i.e., perpendicular to the axis of rotation of the working head) sectional view of a portion of the working head shown in FIG. 1.

DETAILED DESCRIPTION OF THE PREFERRED EMBODIMENT

Figure 1:
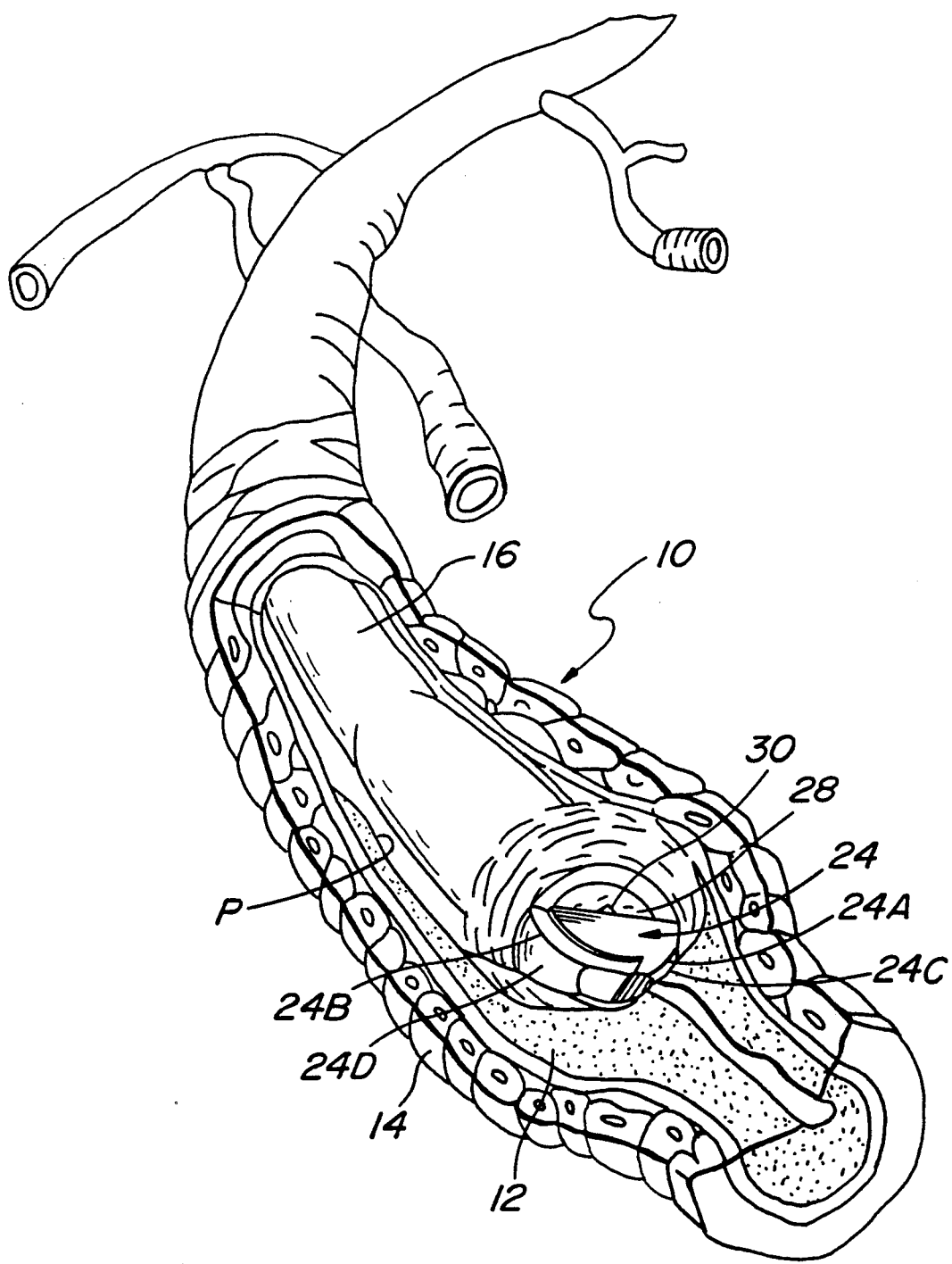
FIG. 1 is a perspective view of a recanalizing catheter having a working head constructed in accordance with this invention opening a restriction in an artery.

Referring now in detail to the various figures of the drawing wherein like reference characters refer to like parts, there is shown at 10 in FIG. 1 a catheter apparatus constructed in accordance with the subject invention. The catheter 10 is particularly suited for recanalizing atherosclerotic deposit-occluded or restricted arteries, but can be used for enlarging the opening through any type of vessel, duct, or lumen within the body of a living being.

The portion of catheter 10 shown in FIG. 1 constitutes its distal end and is shown in the process of opening a restriction 12 in an artery 14. Such arterial restrictions are formed by the deposit of atherosclerotic plaque or some other materials(s), such as wax and/or calcified atheroma, thickened and/or ulcerated intima, etc.

The catheter 10 basically comprises an elongated flexible tubular body member or jacket 16 at the free or distal end 18 of which is located a rotatable working head 24. The working head 24 is generally similar to that described in the '821 patent except for the inclusion of impacting surfaces of differing degrees of aggressiveness of action. Thus, the working head 24 of this invention basically comprises two impacting surfaces 24A and two impacting surfaces 24B which are arranged to be selectively brought into engagement with the material forming the restriction 12 as the catheter's working head is rotated about the catheter's longitudinal axis in either of two rotational directions. The impacting surfaces 24A have a different radius of curvature (and optionally—some rake or clearance) than the impacting surfaces 24B to exhibit respective and different degrees of aggressiveness of restriction opening action, with surfaces 24A being less aggressive in action than surfaces 24B.

The details of the working head 24 and its impacting surfaces 24A and 24B will be described later. Suffice it for now to state that the working head is arranged to be rotated at a high rate of speed, e.g., 10,000 to 200,000 RPM or higher, about the longitudinal axis 25 (FIGS. 3 and 4) of the catheter in one rotational direction (e.g., counterclockwise as viewed in FIGS. 1 and 2) to bring the working head's impacting surfaces 24A into engagement with the material forming the restriction 12. The catheter is then advanced in a longitudinally in a distal direction through the restriction. This action opens the restriction, i.e., forms a passageway P for blood to flow therethrough, in the same manner as described in detail in U.S. the '821 patent. In particular, the passageway P is opened by dilating the stenotic or occluded area (which may or may not be covered by fibrous plaque) and/or selectively removing calcified thrombotic, or fatty tissue unprotected by fibrous plaque while allowing the artery wall to remain intact. The less aggressive action of the working head's impacting surfaces 24A on the material forming the restriction ensures that the passageway P is produced with minimal danger of damage to the tissue of the artery. Once the passageway P has been formed the working head 24 may then be rotated in the opposite rotational direction (e.g., clockwise as viewed in FIGS. 1 and 2), again at a high rate of speed, and withdrawn, i.e., passed in the longitudinally proximal direction, through the passageway P so that its impacting surfaces 24B engage the material contiguous with the previously formed/enlarged passageway to enlarge or dilate it further.

The catheter jacket 16 is formed of any suitable material, e.g., plastic, and has a small outside diameter. In the preferred embodiment shown herein, the outside diameter is approximately 1.5 mm (5 French) or less. This size catheter is merely exemplary. Thus, in accordance with this invention the catheter can be constructed as small as 2 French (0.6 mm). The means for effecting the rotation of the working head is not shown but can comprise any suitably constructed system such as but not limited to those disclosed in the foregoing U.S. Pat. Nos. 4,686,982, 4,747,821, and U.S. application Ser. No. 938,698 filed on Dec. 5, 1986, and entitled "Catheter With Means To Prevent Wear Debris From Exiting," now abandoned.

Irrespective of the construction of the drive system utilized it is coupled to the working head 24 so that the working head is rotated at the high rate of speed by a proximately located motor (not shown). As can be seen clearly in FIGS. 3 and 4 the working head 24 includes a central shank portion or axle 26 projecting proximally therefrom. The axle 26 is supported in a central bore (not shown) of a bushing 28 fixedly mounted at the distal end of the catheter's jacket 16. Like the catheters disclosed in the '821 patent a liquid is preferably passed down through the catheter jacket 16 through four equidistantly spaced grooves (not shown) extending down the central bore of the bushing 28 and exiting at ports 30 (only one of which can be seen in FIG. 1) to aid in the enlargement of the opening in the vessel, duct or lumen. Further still, the liquid which is passed down the catheter can, if desired, be oxygenated to eliminate distal ischemia when the catheter is used for arterial restriction opening procedures. Also, if desired, nitrates, contrast media, or other drugs can be added to the liquid as needed during the procedure.

The details of the working head 24 will now be discussed. The working head 24 basically comprises a convex shaped tip of a generally hemispherical shape and having a pair of generally planar diametrically disposed relieved side surfaces or faces. This structure forms the heretofore identified impacting surfaces 24A and 24B. In particular those impacting surfaces are formed by rounded or radiused edges of a respective pair of cam surfaces 24C and 24D. The cam surfaces themselves are formed by the outer convex (e.g., spherical) surface portions of the working head located between a pair of relieved planar surfaces 24E and 24F. The interface of the cam surface 24C and the relieved surface 24E forms one impacting surface 24A, while the interface of the cam surface 24D and the relieved surface 24F forms the other impacting surface 24A. As can be seen in FIG. 5 the impacting surfaces 24A are rounded (radiused) in a plane perpendicular to the axis of rotation of the working head so that each is not sharp, e.g., is in the range of approximately 0.001 inch to approximately 0.008 inch, although in the scale of FIGS. 1–4 of the drawing they appear to be a sharp line. The portion of each of the relieved surfaces 24E and 24F at their interface with the cam surfaces 24C and 24D, respectively, are further relieved, ground, or cut away to form relieved lip surfaces 24E' and 24F', respectively. The interface of the cam surface 24C and the relieved lip surface 24F' forms one of the aggressive impacting surface 24B, while the interface of the cam surface 24D and the relieved lip surface 24E' forms the other aggressive impacting surface 24B. The aggressive impacting surfaces 24B are also rounded (radiused) in a plane perpendicular to the axis of rotation of the working head so that each is not sharp, e.g., is of a radius of 0.0005 inch to approximately 0.002 inch, although even in the scale of the enlarged sectional view of FIG. 5, they appear to be a sharp line.

The relieved surfaces 24E and 24F taper toward each other in the direction toward the distal end of the working head, with the maximum space between the relieved surfaces being slightly larger than the diameter of the working head shaft or axle. The flatted or relieved surfaces 24E and 24F are preferably within the range of 0 to 10 degrees negative rake to the radius R forming the spherical cam surfaces 24C and 24D, while the flatted or relieved surfaces 24E' and 24F' may be at a more aggressive angle, e.g., from three degrees negative to ten degrees positive rake, to radius R of the cam surfaces 24C and 24D. Moreover, if desired, the clearance of the working head cam surfaces contiguous with the non-aggressive and/or aggressive impacting surfaces 24A and 24B, respectively, may be configured as desired, depending upon the desired application of the instrument.

By virtue of the shape of the working head, the free or open end ports 30 of two diametrically opposed grooves are uncovered or exposed by the relieved surfaces 24E and 24F to enable fluid passing through those grooves to exit the ports in the same manner as described in the '821 patent. As will be appreciated by those skilled in the art, since the working head rotates, the relieved surfaces of the working head sequentially cover and uncover diametrically opposed ports at the distal ends of the grooves. This action breaks up the fluid streams exiting from those ports into segments or slugs which are distributed in a generally hemispherical pattern about the working head. The liquid slugs have some radial component and develop tremendous momentum as they are flung outward toward the artery wall. The momentum of the slugs is transferred to the artery wall thereby forcing the artery wall laterally outward in all radial directions thereby dilating the vessel as described in the aforementioned patent.

The rotation of the working head about the longitudinal axis 25 also produces a powerful toroidal shaped vortex contiguous with the working head. The vortex has the effect of recirculating any particles that are broken off from the restriction by the impact of the rotating working head with the material forming the restriction. Thus, if the material forming the restriction is such that particles are broken away, they are circulated by the vortex and carried back into the rotating working head where they are progressively reduced in size to the point where they can safely flow distally.

It must be pointed out at this juncture a catheter constructed in accordance with this invention can be utilized with its working head rotating in the rotational direction to bring the more aggressive impacting surfaces 24B into engagement with the material forming the restriction in the first instance (i.e., without prior use of the less aggressive impacting surfaces 24A). Thus, in some cases it may not be necessary to first open the restriction somewhat by the use of the less aggressively acting impacting surfaces 24A of the working head. Further still, even if the restriction is first opened by the use of the less aggressively acting impacting surfaces 24A the passage of the working head through the passageway P while rotating in the rotational direction, e.g., clockwise in FIGS. 1 and 2, to bring the more aggressively acting impacting surfaces 24B into engagement with the material forming the restriction at the passageway P can be accomplished from either the proximal to distal direction or vice versa.

It must also be pointed out that while the working head shown and described herein includes two of each of the impacting surfaces, 24A and 24B such a construction is not required. Thus, the working head may be constructed to include only one impacting surface of each type, i.e., one surface 24A and one surface 24B, or more than two of each such surface, depending upon the application desired.

Moreover, as mentioned earlier, the working head and/or an instrument making use of the working head of this invention can be utilized to destroy a stone or other hard body located within the body of a living being. That action is accomplished by placing the instrument so that the working head is adjacent the stone, whereupon the working head is rotated in either rotational direction, as desired, to create the vortex flow and thereby pull the stone into engagement with the impacting surfaces 24A or 24B (depending upon the direction of rotation). This action breaks the stone into particles which are recirculated by the vortex flow back into engagement with the impacting surfaces so that they are further reduced in size (pulverized).

As should be appreciated by those skilled in the art, the selective engagement by either the less aggressive impacting surfaces or the more aggressive impacting surfaces (such as is preferably accomplished by the selection of the desired direction of rotation of the head to bring that (those) impacting surface(s) into engagement with the tissue or material forming the restriction, be it a partial or total occlusion), provides the physician with a powerful modality for revascularizing an artery. Thus, rotation of the working head in one rotational direction about the longitudinal axis of the device to bring the less aggressive impacting surfaces into action can be used to revascularize an artery having relatively soft material deposits, e.g., fatty tissue, thrombus, etc., therein, while rotation of the working head in the opposite rotational direction to bring the more aggressive impacting surfaces into action can be used to effect recanalization of relatively hard deposits or tissue, e.g., calcific tissue, fibrous cap tissue, etc., which require more energy to effect the pulverization thereof.

Without further elaboration, the foregoing will so fully illustrate our invention that others may, by applying current or future knowledge, readily adopt the same for use under various conditions of service.

We claim:

1. A method of recanalizing an artery located in the body of a living being utilizing an instrument comprising an elongated body portion and a moveable working head, said artery being partially or fully occluded by material located therein, said material comprising at least one portion made up of a relatively soft component or a relatively hard component, said working head being arranged for rotation about a longitudinal axis of said instrument in either of two opposite rotational directions and comprising a first non-sharp, impacting surface exhibiting a first predetermined aggressiveness of action when engaging material comprising said relatively soft component, and a second non-sharp, impacting surface exhibiting a second and greater predetermined aggressiveness of action when engaging material comprising said relatively hard component, said method comprising introducing said instrument into said body so that said working head is adjacent said material to bring one of said impacting surfaces into engagement with said material, selectively rotating said working head about said axis in one of said rotational directions, said rotational direction being selected depending upon which of said impacting surfaces is to be brought into engagement with said material, whereupon if said material to be engaged by said working head comprises said relatively soft material said working head is rotated in the rotational direction to bring said first impacting surface into engagement with said material and if said material to be engaged by said working head comprises said relatively hard material said working head is rotated in the opposite rotational direction to bring said second impacting surface into engagement with said material.

2. The method of claim 1 wherein said relatively soft component comprises fatty tissue.

3. The method of claim 1 wherein said relatively soft component comprises thrombus.

4. The method of claim 1 wherein said relatively hard component comprises calcific tissue.

5. The method of calim 1 wherein said relatively hard material comprises fibrous cap tissue.

6. The method of claim 1 wherein said material comprises a portion of said relatively soft component and a portion of said relatively hard component, said method including the steps of rotating said working head in said one direction for bringing said first impacting surface into engagement with said relatively soft component, and rotating said working head in said opposite direction for bringing said second impacting surface into engagement with said relatively hard component.

7. The method of claim 6 wherein said relatively soft component comprises fatty tissue.

8. The method of claim 6 wherein said relatively soft component comprises thrombus.

9. The method of claim 6 wherein said relatively hard component comprises calcific tissue.

10. The method of claim 6 wherein said relatively hard material comprises fibrous cap tissue.

11. A method of recanalizing an artery located in the body of a living being utilizing an instrument comprising an elongated body portion and a movable working head, said artery being partially of fully occluded by material located therein, said material comprising at least one relatively soft component and at least one relatively hard component, said working head being arranged for rotation about a longitudinal axis of said instrument and comprising a first non-sharp, impacting surface exhibiting a first predetermined aggressiveness of action when engaging material comprising said at least one relatively soft component, and a second non-sharp, impacting surface exhibiting a second and greater predetermined aggressiveness of action when engaging material comprising said at least one relatively hard component, said method comprising the steps of introducing said instrument into said body so that said working head is adjacent said material including said at least one relatively soft component, rotating said working head about said axis and bringing said first impacting surface into engagement with said at least one relatively soft component, and positioning the working head adjacent the material including said at least one relatively hard component, rotating said working head about said axis and bringing said second impacting surface into engagement with said at least one relatively hard component.

12. The method of claim 11 wherein said relatively soft component comprises fatty tissue.

13. The method of claim 12 wherein said relatively hard component comprises calcific tissue.

14. The method of claim 12 wherein said relatively hard material comprises fibrous cap tissue.

15. The method of claim 11 wherein said relatively soft component comprises thrombus.

16. The method of claim 15 wherein said relatively hard component comprises calcific tissue.

17. The method of claim 15 wherein said relatively hard material comprises fibrous cap tissue.

* * * * *